United States Patent [19]

Halpern

[11] 4,456,721

[45] Jun. 26, 1984

[54] FLAME-RETARDED ACRYLONITRILE-BUTADIENE-STYRENE COPOLYMER COMPOSITIONS COMPRISING BIS(BETA-PENTABROMOPHENOX-YETHYL) SUCCINATE

[75] Inventor: Yuval Halpern, Skokie, Ill.

[73] Assignee: Borg-Warner Chemicals, Inc., Parkersburg, W. Va.

[21] Appl. No.: 446,123

[22] Filed: Dec. 2, 1982

[51] Int. Cl.³ .............................................. C08K 5/11
[52] U.S. Cl. ..................................... 524/288; 560/193
[58] Field of Search ......................... 524/288; 560/193

[56] References Cited

U.S. PATENT DOCUMENTS

| | | | |
|---|---|---|---|
| 1,991,391 | 2/1935 | Izard | 560/193 |
| 2,394,512 | 2/1946 | Coleman et al. | 560/193 |
| 2,765,224 | 10/1956 | Lambrech | 560/193 |
| 3,123,580 | 3/1964 | Dunn et al. | 560/193 |
| 3,275,596 | 9/1966 | Klug et al. | 524/288 |
| 3,317,568 | 5/1967 | Wygant et al. | 524/307 |
| 3,386,935 | 6/1968 | Jackson et al. | 260/26 |
| 3,830,766 | 8/1974 | Praetzel et al. | 524/371 |

FOREIGN PATENT DOCUMENTS 590635  1/1960  Canada .

Primary Examiner—Veronica P. Hoke
Attorney, Agent, or Firm—Richard J. Schlott

[57] ABSTRACT

Compositions comprising ABS and bis(beta-pentabromophenoxyethyl) succinate have good flame retardance and are self-extinguishing in the UL-94 vertical burn test. The compositions may be further compounded with a conventional synergist such as antimony oxide.

5 Claims, No Drawings

FLAME-RETARDED ACRYLONITRILE-BUTADIENE-STYRENE COPOLYMER COMPOSITIONS COMPRISING BIS(BETA-PENTABROMOPHENOXYETHYL) SUCCINATE

BACKGROUND OF THE INVENTION

This invention is directed to flame-retarded acrylonitrile-butadiene-styrene copolymer compositions comprising bis(beta-pentabromophenoxyethyl) succinate.

Highly brominated compounds such as the tetrabromophenyl ethers and perbrominated biphenyl compounds are well-known flame retardants for a variety of thermoplastic resins. Although the flame retarding behavior of such compounds is adequate for many materials, the tendency to migrate and to be exuded from the resin during processing, particularly where the compounds are employed at high concentrations in the resin, are distinct disadvantages. Methods in the art for overcoming the tendency of flame retardants to migrate during processing have included incorporating the brominated moiety into a polymeric structure, such as by grafting a bromine-containing molecule onto an existing substrate, by directly brominating the substrate or by copolymerizing a suitable bromine-containing monomer in the preparation of the thermoplastic. As an alternative, flame retardant molecules have been sought which possess an appropriate combination of solubility in the thermoplastic resin, adequate stability at resin processing temperatures, and sufficient ability to retard burning without resort to an inordinately high concentration in the resin. As will be appreciated by those skilled in the art, the great proliferation of compounds available for use as a flame retardants has come about in part because no single compound possesses a balance of these characteristics that is adequate for use in every thermoplastic resin. Most flame-retardant compounds are known to be useful in a very limited class of thermoplastic resins, and the search for compounds having more effective balance of characteristics continues.

SUMMARY OF THE INVENTION

This invention is directed to a new flame retardant for ABS resins, and more particularly to flame-retarded compositions comprising ABS and bis(beta-pentabromophenoxyethyl) succinate, a compound having the following structure:

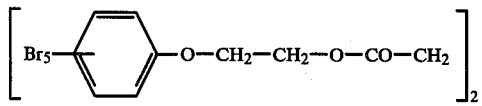

This compound a di-pentabromophenoxyethyl ester of succinic acid, is thermally stable at temperatures well above the temperatures employed for melt processing ABS resins, is readily dispersible for maximum effectiveness in flame retardance, and has a lower tendency to migrate due to its high molecular weight and solubility in the resin.

DETAILED DESCRIPTION OF THE INVENTION

The flame retardant compound of this invention is bis(beta-pentabromophenoxyethyl) succinate. It may be prepared by the ethoxylation of pentabromophenol, a commercially available compound, with ethylene oxide to provide beta-pentabromophenoxyethanol. The ester is prepared by esterifying two moles of the beta-pentabromophenoxyethanol with succinic anhydride.

ABS resins are flame retarded when compounded with bis(beta-pentabromophenoxyethyl) succinate. The compound of this invention is somewhat more effective than many brominated compounds, imparting self-extinguishing characteristics to ABS resins at reduced concentrations. When compounded with a conventional synergist such as antimony oxide, substantial flame retardance results when as little as 10 wt.% of the brominated compound of this invention is present, and amounts above about 12 wt.% are effective in providing self-extinguishing compositions. Amounts as great as 50 wt% bis(beta-pentabromophenoxyethyl) succinate and more will also be effective in flame-retarding an ABS resin. However, as a practical matter levels far above the minimum necessary to provide effective flame retardance are uneconomical and are not preferred. The preferred compositions will comprise from 10 to 40 wt% by weight (of the total composition) and more preferably from 10 to 30% by weight of the brominated compound of this invention. Conventional brominated flame retardants will be employed in larger amounts, and frequently amounts as great as 25 wt%, are needed to provide self-extinguishing compositions.

The ABS resins that are usefully flame retarded by the compound of this invention are widely available commercially and include graft copolymers of acrylonitrile and styrene on a diene homopolymer or copolymer rubber substrate. Also included are the variety of analogous resins wherein all or a portion of the styrene component may be replaced with other vinyl aromatic monomers such as alpha methyl styrene and the like, and those wherein all or a portion of the acrylonitrile is replaced with methacrylonitrile, methylmethacrylate (MABS and MBS) and the like. Further analogs including the graft copolymers of styrene and acrylonitrile or the like on an acrylate rubber substrate are also useful. Although the ABS resins are described as graft copolymer resins, a variety of analogs are known wherein a rigid copolymer such as SAN or a methylmethacrylate-acrylonitrile-styrene copolymer is blended with a rubbery polymer such as a high rubber content styrene-acrylonitrile-butadiene (ABS) graft polymer. As used herein, the term ABS is thus intended to incorporate the wide variety of engineering thermoplastic resins recognized in the art as ABS resins.

The invention will be better understood by consideration of the following examples.

EXAMPLE 1

Synthesis of beta-pentabromophenoxyethanol

Into four one-pint citrate bottles were placed 180 ml deionized water, 2.3 g NaOH, and 22 g pentabromophenol. A magnetic stirring bar was added to each, and nitrogen was bubbled into each of the bottles for 3 min. The bottles were then sealed, contents were stirred while liquid ethylene oxide (12 ml) was injected into each bottle through the seals in 2 ml portions over a 5½ hr. period. The mixtures were stirred at room temperature for an additional 17 hrs. The bottles were opened and the combined solid product was collected by filtration. The white product was washed twice with deionized water, dried in a vacuum oven at 76° C. to constant weight, then recrystallized from 850 ml toluene to give 39 g of pentabromophenoxy ethanol, m.p.=163° C.

EXAMPLE 2

Synthesis of bis(beta-pentabromophenoxyethyl) succinate

A 250 ml, three-necked round-bottom flask equipped with a thermometer, Dean-Stark trap and magnetic stirrer was charged with 175 ml dry toluene and heated in an oil bath to 70° C. Dry beta-pentabromophenoxyethanol (32 gr, 0.06M) was charged to the flask, followed by 3 gr (0.03M) dry succinic anhydride and 4 drops of concentrated sulfuric acid. The reaction mixture was heated to reflux. After ca.0.5 ml (0.03M) water was collected in the Dean-Stark trap, the reaction mixture was cooled to room temperature and then chilled for one hour. The product separated and was collected by filtration, washed twice with 100 ml cold toluene and dried to a constant weight at 70° C. under vacuum. Yield 30 gr (0.05M, 83%), m.p.=194° C. The structure of the product as bis(beta-(pentabromophenoxy)ethyl) succinate was confirmed by carbon-13 NMR (in pyridine $d_5$) and IR. The elemental analysis results were in agreement with the proposed product. Calculated for bis(beta-pentabromophenoxyethyl) succinate ($C_{20}H_{12}Br_{10}O_6$) %C=20.94, %H=1.05, %Br=69.94 found: %C=20.97, %H=1.04, %Br=69.55.

EXAMPLES 3-6

Flame-retarded ABS Compositions

The flame retardant of Example 2 was compounded with ABS, antimony oxide and various lubricants and additives to demonstrate the flame retardant character of such compositions. The blends, summarized in Table I, were formed by combining the indicated materials in a Brabender Plasticorder fitted with a mixing head at 350° F., cooling the samples, then compression molding at 350° F. to provide test specimens. The compositions and flame retardance test results are summarized in Table I.

TABLE I

| | | Flame Retarded ABS Blends | | | |
|---|---|---|---|---|---|
| Ex. No.: | | 3 | 4 | 5 | 6 |
| Compositions | | | | | |
| ABS[1] | pbw | 100 | 100 | 100 | 100 |
| FR[2] | pbw | 18 | 24 | 24 | 17 |
| FR | wt % | 14.9 | 18.7 | 17.8 | 13.8 |
| $Sb_2O_3$ | pbw | 6.7 | 4 | 4 | 6.4 |
| Other | pbw | 5[3] | — | 5[7] | — |
| Lubricants | pbw | 0.8[4] | 0.5[5] | 2[6] | — |
| Properties | | | | | |
| LOI[8] | | — | 29.1 | 26.9 | — |
| UL-94[9] | | V-0 | V-0 | V-0 | V-0 |
| Ave. burn, sec. | | 0.8 | 0 | 0 | — |
| Max. burn, sec. | | 2 | 0 | 0 | — |

[1]ABS = Cycolac 201 ABS from Borg-Warner Chemicals, Inc.
[2]FR = bis(beta-pentabromophenoxyethyl) succinate (Example 2)
[3]5 parts chlorinated polyethylene from Dow Chemical Co.
[4]0.8 parts magnesium stearate lubricant
[5]0.5 parts Acrawax C lubricant from Glyco Chemicals, Inc.
[6]2 parts barium stearate lubricant
[7]5 parts, includes 1 pbw magnesium oxide and 4 pbw Titanium dioxide.
[8]LOI = limiting oxygen index
[9]UL-94 = vertical burn, with ave. and maximum burn times in seconds.

It will be apparent that excellent, self-extinguishing flame retardance character is imparted to ABS when compounded with bis(beta-pentabromophenoxyethyl) succinate. The composition of Example 4 had a notched impact value of 1.1 ft lbs/in notch and a heat distortion temperature at 264 psi of 171° F., demonstrating that the ABS compositions containing the flame retardant of this invention are neither embrittled nor greatly plasticized thereby.

The invention disclosed will be seen to be flame-retarded ABS compositions comprising ABS and bis(-beta-pentabromophenoxyethyl) succinate. The compositions will comprise from 10 to 40 wt% and more preferably from 10 to 30 wt% of bis(beta-pentabromophenoxyethyl) succinate, based on final composition of resin and flame retardant. The compositions may further comprise from 3 to 15 parts per hundred parts by weight ABS of a conventional synergist for bromine-containing flame retardants such as antimony oxide or the like, as well as lubricants, stabilizers, dyes, pigments, fillers, fibrous reinforcing materials such as glass fiber and the like as is well known in the ABS compounding art. The compositions of this invention, which have been illustrated by way of the accompanying and non-limiting examples, are useful as flame retarded engineering thermoplastic resins and may be further modified through compounding and formulating as will be recognized by those skilled in the art of resin molding and processing without departing from the spirit and scope of the invention.

I claim:

1. A flame-retarded composition comprising an acrylonitrile-butadiene-styrene resin and a flame-retarding amount of bis(beta-pentabromphenoxyethyl) succinate.

2. A flame-retarded composition comprising from 90 to 60 wt% of an acrylonitrile-butadiene-styrene and correspondingly from 10 to 40 wt% bis (beta-pentabromophenoxyethyl) succinate.

3. The composition of claim 2 further comprising a synergist for bromine-containing flame retardants.

4. The composition of claim 2 further comprising antimony oxide.

5. The composition of claim 2 further comprising from 3 to 15 parts by weight antimony oxide per hundred parts by weight an acrylonitrile-butadiene-styrene copolymer.

* * * * *